(12) United States Patent
Kurth (10) Patent No.: US 12,245,987 B2
(45) Date of Patent: Mar. 11, 2025

(54) BABY MOUTH SIMULATOR

(71) Applicant: MAM Baby AG, Wollerau (CH)

(72) Inventor: Elisabeth Kurth, Radebeul (DE)

(73) Assignee: MAM Baby AG, Wollerau (CH)

( * ) Notice: Subject to any disclaimer, the term of this patent is extended or adjusted under 35 U.S.C. 154(b) by 457 days.

(21) Appl. No.: 16/640,471

(22) PCT Filed: Aug. 21, 2018

(86) PCT No.: PCT/EP2018/072494
§ 371 (c)(1),
(2) Date: Feb. 20, 2020

(87) PCT Pub. No.: WO2019/038255
PCT Pub. Date: Feb. 28, 2019

(65) Prior Publication Data
US 2020/0360580 A1 Nov. 19, 2020

(30) Foreign Application Priority Data
Aug. 21, 2017 (DE) ................ 10 2017 119 034.1

(51) Int. Cl.
*A61J 13/00* (2006.01)
*A61M 1/00* (2006.01)
(Continued)

(52) U.S. Cl.
CPC ............ *A61J 13/00* (2013.01); *A61M 1/06* (2013.01); *A61M 1/064* (2014.02);
(Continued)

(58) Field of Classification Search
CPC ........ A61M 1/06; A61M 1/064; A61M 1/062; A61M 1/066; A61M 1/0697; A61M 1/75; A61B 5/683; A61J 13/00
See application file for complete search history.

(56) References Cited

U.S. PATENT DOCUMENTS

| 949,414 A | * | 2/1910 | Cunningham | ........ A61M 1/062 D2/709 |
| 3,822,703 A | * | 7/1974 | Davisson | .......... A61M 1/06935 604/75 |

(Continued)

FOREIGN PATENT DOCUMENTS

| CA | 3034952 A1 * | 3/2018 | .......... A61M 1/0037 |
| CN | 1958084 A | 5/2007 | |

(Continued)

OTHER PUBLICATIONS

Office Action issued in China Counterpart Patent Appl. No. 201880056024.5, dated Mar. 29, 2022, along with an English translation thereof.

(Continued)

*Primary Examiner* — Scott J Medway
(74) *Attorney, Agent, or Firm* — GREENBLUM & BERNSTEIN, P.L.C.

(57) ABSTRACT

The invention relates to a baby mouth simulator for the female breast, comprising a receiving space for the lactated milk. The baby mouth simulator further comprises a milking sleeve, by means of which a manual milking pressure causing a lactation can be carried out to the nipple and the adjoining regions. The aim of the baby mouth simulator is to improve the effectivity of the method of a manual generation of a lactation of the female breast. This aim is achieved in that the milking sleeve is designed as a dual sleeve, wherein an inner sealing sleeve, which seals the receiving space with respect to the areola when used as intended, and a fixing sleeve, which mechanically fixes the baby mouth simulator on the breast when used as intended, is provided, and the receiving space is designed as a vacuum space.

11 Claims, 10 Drawing Sheets

(51) Int. Cl.
*A61M 1/06* (2006.01)
*A61M 39/24* (2006.01)

(52) U.S. Cl.
CPC ............ *A61M 1/0697* (2021.05); *A61M 1/60* (2021.05); *A61M 1/64* (2021.05); *A61M 39/24* (2013.01); *A61M 2205/02* (2013.01); *A61M 2210/1007* (2013.01)

(56) References Cited

U.S. PATENT DOCUMENTS

| | | | | |
|---|---|---|---|---|
| 4,680,028 | A * | 7/1987 | Stuart | A61M 1/064 604/74 |
| 4,740,196 | A * | 4/1988 | Powell | A61M 1/06 604/74 |
| 4,870,977 | A * | 10/1989 | Imonti | A61F 15/008 623/7 |
| 6,152,896 | A * | 11/2000 | Bachman | A61M 1/81 604/74 |
| 6,440,100 | B1 * | 8/2002 | Prentiss | A61M 1/067 604/326 |
| 6,706,012 | B2 * | 3/2004 | McKendry | F04B 45/041 604/74 |
| 6,821,185 | B1 * | 11/2004 | Francis | A61M 1/067 450/36 |
| 6,887,217 | B1 * | 5/2005 | Logan | A61M 1/064 604/74 |
| 6,962,519 | B1 * | 11/2005 | Clark | A61J 13/00 450/39 |
| 7,607,965 | B1 * | 10/2009 | Frazier | A61J 15/0011 604/74 |
| 8,070,715 | B2 * | 12/2011 | Quackenbush | A61M 1/06 604/74 |
| 10,617,806 | B2 * | 4/2020 | Bartlett | A61M 1/06 |
| 10,632,238 | B1 * | 4/2020 | Hodges | A61J 11/002 |
| 10,925,719 | B2 * | 2/2021 | Kaplan | A61F 2/105 |
| 11,206,875 | B2 * | 12/2021 | Morrow Contreras | A41C 3/065 |
| 11,478,576 | B2 * | 10/2022 | John | F04B 49/065 |
| 2002/0198489 | A1 * | 12/2002 | Silver | A61M 1/064 119/14.47 |
| 2008/0039781 | A1 * | 2/2008 | Bjorge | A61M 1/067 604/74 |
| 2008/0287037 | A1 * | 11/2008 | Solberg | A61M 1/067 450/36 |
| 2009/0030368 | A1 * | 1/2009 | Silver | A61J 13/00 604/74 |
| 2009/0194116 | A1 * | 8/2009 | Pacini | A61J 13/00 128/890 |
| 2010/0179472 | A1 * | 7/2010 | Weston | A61M 1/732 604/67 |
| 2012/0004604 | A1 | 1/2012 | Riette et al. | |
| 2012/0035536 | A1 * | 2/2012 | Gottenbos | A61M 1/066 604/74 |
| 2015/0065994 | A1 * | 3/2015 | Fridman | A61M 1/066 604/74 |
| 2015/0157776 | A1 | 6/2015 | Brittner | |
| 2016/0206794 | A1 | 7/2016 | Makower et al. | |
| 2016/0287769 | A1 | 10/2016 | Makower et al. | |
| 2016/0303298 | A1 | 10/2016 | Makower et al. | |
| 2016/0310649 | A1 | 10/2016 | Makower et al. | |
| 2016/0310650 | A1 | 10/2016 | Makower et al. | |
| 2018/0001002 | A1 | 1/2018 | Makower et al. | |
| 2019/0240386 | A1 * | 8/2019 | Larsson | A61M 1/06 |

FOREIGN PATENT DOCUMENTS

| | | | |
|---|---|---|---|
| CN | 101843928 A | 9/2010 | |
| CN | 102065922 A | 5/2011 | |
| DE | 102012018903 A1 * | 3/2014 | ............ A61M 1/06 |
| DE | 102014103567 | 9/2015 | |
| DE | 102014103567 A1 | 9/2015 | |
| JP | S40-036387 | 12/1965 | |
| JP | S52-171191 | 12/1977 | |
| JP | 2002-085552 | 3/2002 | |
| JP | 2017-509379 | 4/2017 | |
| WO | WO-2009015206 A1 * | 1/2009 | .......... A61H 9/0057 |
| WO | 2016/014469 | 1/2016 | |

OTHER PUBLICATIONS

Office Action issued in Japan Counterpart Patent Appl. No. 2020-510558, dated Apr. 12, 2021, along with an English translation thereof.

Int'l Search Report (Forms PCT/ISA/220 & 210) conducted in Int'l Appln. No. PCT/EP2018/072494 (Dec. 10, 2018).

Int'l Written Opinion (Form PCT/ISA/237) conducted in Int'l Appln. No. PCT/EP2018/072494 (Dec. 10, 2018).

* cited by examiner

BABY MOUTH SIMULATOR

BACKGROUND

1. Field of the Invention

The invention relates to a baby's mouth simulator for the female breast, having a receptacle for the lactated milk. It also has a milking cuff with a flexible part with which the baby's mouth simulator can be positioned on the female breast. This milking cuff is configured in a manner such that a manual milking pressure which brings about lactation can be exerted on the nipple and the adjoining regions.

2. Description of the Background

DE 10 2014 103 567 A1 discloses a milk expressing module for the female breast. This has a collecting vessel for the lactated milk. It describes various methods for bringing about a milking movement or of exerting a milking pressure. These consist of a "thumb-over-finger-under method" or a "two-to-ten-finger method", hereinafter designated as "spread finger methods", and a "five-finger method", hereinafter designated as a "pointed finger method". With both methods, rapid and sustained ejection of milk is achieved in a physiological manner. The method for producing lactation as well as the function and action of the milk expressing module are described in detail in that specification.

That known milk ejection module is configured as a milking cuff comprising an opening for the lactated milk. The milking cuff has a flexible part with which it can be positioned and sealed on the female breast. In this regard, it is configured in a manner such that, a manual milking pressure which brings about lactation can be exerted on the nipple and the adjoining regions, wherein a valve is disposed at the opening. It has been shown that in practice, when lactation is produced with the milk expressing module, a portion of the milk does not reach the collecting vessel and frequently, the negative pressure is lost.

SUMMARY

Thus, the aim of the invention is to improve the efficiency of the method for manually producing lactation of the female breast. The efficiency here is determined by an increase in the collected quantity of milk over a short period, in particular both by means of an improvement in the manual action, longer retention of the negative pressure as well as preventing losses.

A baby's mouth simulator in accordance with the invention of the type mentioned above proposes that the milking cuff is configured as a double cuff, wherein an inner sealing cuff which seals the receptacle against, the areola when used appropriately and a fixation cuff which mechanically fixes the baby's mouth simulator on the breast when used appropriately are provided, and in that the receptacle is configured as a vacuum chamber.

A baby's mouth simulator of this type is suitable both when using the pointed finger and also the spread finger method. In the pointed finger method, the fingertips of one hand are held axially with respect to the nipple so that in this manner, a milking pressure can be exerted on the nipple and the adjoining regions through a wall surrounding the receptacle. With the spread finger method, the fingers are held radially or tangentially to the nipple. In both methods, the receptacle can be deformed from the outside with the fingers, whereupon the application of a mechanical pressure corresponds to stimulation by an infant's mouth cavity. Here, the inner sealing cuff—which seals the receptacle against the breast—is positioned on the breast, in particular in the region of the areola. The receptacle is compressed by the pressure of the fingers, some air escapes from the receptacle and a negative pressure or slight vacuum is produced. This corresponds to an infant's suckling. In this manner, by means of the baby's mouth simulator in accordance with the invention, all of the important factors for bringing about lactation in a natural way and with characteristic emotional feedback can be simulated.

The outer fixation cuff does not need to have a sealing action. Rather more, its primary purpose is to position the baby's mouth simulator on the breast and thus to bring about mechanical fixation. Thus, for example, it is possible to press the fixation cuff onto the breast with one hand and to carry out the milking movement with the other hand. However, it is also possible to express milk with both hands, wherein in this regard, the fingers or the ball of the thumb are placed on the fixation cuff, whereupon the baby's mouth simulator is mechanically fixed.

Because the fixation cuff does not need to have a sealing function, but is tasked with fixing the baby's mouth simulator on the breast, it may have a variety of shapes which are suitable for carrying out this task. However, in one embodiment, the fixation cuff is larger than the sealing cuff (15) and surrounds the sealing cuff.

In one embodiment, the receptacle has an opening which is provided with a valve, in particular a one-way valve, which in particular is configured as a lip valve. In this manner, the air in the receptacle can escape through the valve when the receptacle is compressed. When the fingers release the receptacle again, because of the flexible material, it endeavours to return to its original shape, whereupon the vacuum is produced when the valve is closed, which can occur particularly easily when configured as a one-way valve. In this regard, being produced as a lip valve, the soft resilient material which is used means that this is a particularly simple way of producing this embodiment.

In a further embodiment, a reinforcing ring is provided which surrounds the receptacle. This reinforcing ring essentially acts to provide mechanical protection of the nipple, because it keeps the area around the nipple open.

The baby's mouth simulator may also be configured in two parts. In this manner, on the one hand, this makes manufacture easier. This also makes it easier to use different materials.

The baby's mouth simulator may be configured in a manner such that the flexible part consists of a soft resilient material. A material of this type means that the receptacle can be deformed and sealed in a particularly appropriate manner.

In a further embodiment of the invention, the parts of the baby's mouth simulator consist of different materials. In this manner, it is possible to combine soft resilient materials with stiffer materials.

In one embodiment, a nipple protecting member is provided which can be inserted into the receptacle. This nipple protecting member—in similar manner to the reinforcing ring described above—protects the nipple from too fierce a milking movement. The nipple protecting ring may also be provided in addition to the reinforcing ring or as an alternative thereto. In particular, the nipple protecting member may be used in a baby's mouth simulator provided with external protrusions for the pointed finger method, as described below, because with this solution, there is no reason to attach a reinforcing ring.

In one embodiment of the invention, the nipple protecting member may also be used for a plurality of functions. In this regard, it is configured in a manner such that it can be inserted into the vacuum chamber in a sealed manner and the sealing cuff is connected to the nipple protecting member.

The baby's mouth simulator may also be configured such that the outside of the receptacle is provided with protrusions in which parts of the fingers of a hand can be accommodated. These protrusions form a kind of glove for fingers. They are configured in a manner such that the female breast/areola can be gently cupped with the fingers of one hand or both hands through the wall of the receptacle and a manual milking pressure causing lactation can be exerted with the fingers on the nipple and the adjoining regions.

In this regard, the protrusions should be configured in a manner such that at least the fingertips of the hand can be accommodated therein and the protrusions surround the receptacle.

In order to produce a baby's mouth simulator which can be used both for the spread finger method and also for the pointed finger method, openers which are stiffer compared with the protrusions are provided, which can be inserted into the protrusions instead of the fingertips. Without these openers, then, the baby's mouth simulator can be used for the pointed finger method. If the openers are inserted into the protrusions, then this arrangement may also be used for the spread finger method.

In one embodiment, a collecting container can be connected to the receptacle. The lactated milk can then flow into this collecting container. Advantageously, the same pressure is provided in the collecting container as in the receptacle, so that the milk can flow without an intermediate valve or pump.

In the case in which no pressure equilibrium can be set between the receptacle and collecting container, the valve or a second valve is disposed between the receptacle and the collecting container.

Advantageously, the collecting container is provided with an arm cuff, in particular for fastening to the wrist or the forearm. In this manner, the collecting container can be held comfortably.

It is also possible to connect a collecting bag, which may have a mechanical vibrator, to the baby's mouth simulator. By means of a vibrator of this type, a mechanical vibration can be introduced into the breast. This promotes the secretion of oxytocin, the let-down reflex hormone.

BRIEF DESCRIPTION OF THE DRAWINGS

The invention will now be explained in more detail with the aid of exemplary embodiments. The accompanying drawings show.

DETAILED DESCRIPTION

In respect of the secretion of mother's milk, three effects are known to cause mother's milk to come out of the breast:

A) In the breast itself, an internal pressure which is caused by the action of oxytocin supplied via the blood vessels. In this regard, oxytocin acts to instantly contract the small muscles which surround the milk-producing cells (alveolae). This effect is also known as the let-down reflex. It is brought about most strongly and positively influenced by stimulation of the nipple with simultaneous relaxation, warmth, freedom from anxiety and from pain, and gentle massage at all appropriate points of the mother's body. An important distinction between this and the effects mentioned below is that the milk will only flow when the milk sacs are internally compressed. Without oxytocin, there would be only a little secretion of milk, even if the breast is very full and suckling is strong.

B) A further effect which causes milk to come out of the breast is the exertion of a significant mechanical pressure on the female breast, which is hereinafter described as the milking pressure because it bears a resemblance to causing milk to flow when milking by hand in dairy farming. On the one hand (variation B1), this pressure can be produced completely naturally by the child making a milking chewing movement on the areola and the nipple with the aid of the gums, tongue, cheeks and jaw. On the other hand, a very similar pressure to that generated by the child (variation B1) can be exerted by the mother, making milking movements with the fingers (variation B2) on the areola. When breastfeeding, variation B2 can be used to support variation B1. This rhythmic milking pressure, together with an active let-down reflex (effect A), is alone sufficient to empty full breasts in a short time. In variation B2, the milk has to be collected, because the up to 20 milk ducts are distributed over the entire tip of the nipple and the milk can spray out in all directions over several metres.

C) The third known effect which brings about the secretion of milk is the negative pressure or suction exerted on the breast by the infant. This effect is exploited by conventional milk pumps. Because the effects of the B variations are not present or are barely present, a negative pressure of up to 300 mm Hg is employed, which can damage the breast. However, an infant produces a negative pressure of only 55 to 150 mm Hg.

These three effects A, B and C may cooperate in different manners to result in the secretion of milk.

In the case in which an infant is fed directly at the breast, all three effects A, B and C work together. This means that a healthy infant, when effect A acts, brings about effect C by suckling, and at the same time brings about effect B1 described above with the gums, tongue etc.

Figure 1:
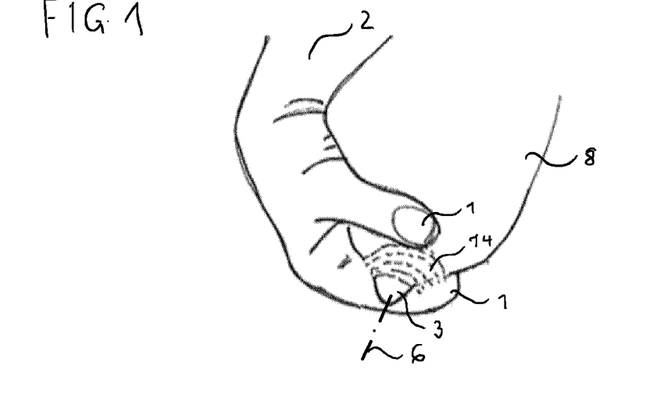
FIG. 1 an application of the spread finger method using one hand.
Figure 2:
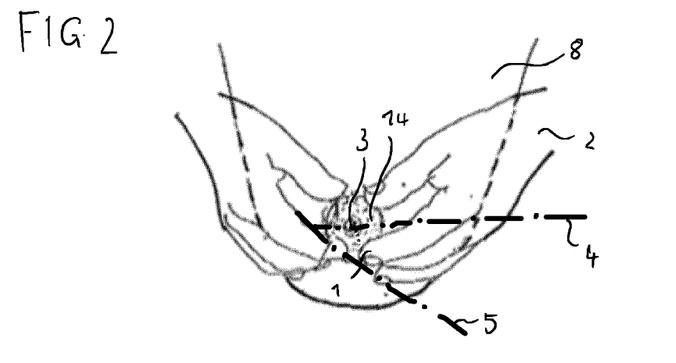
FIG. 2 an application of the spread finger method using two hands.
Figure 3:
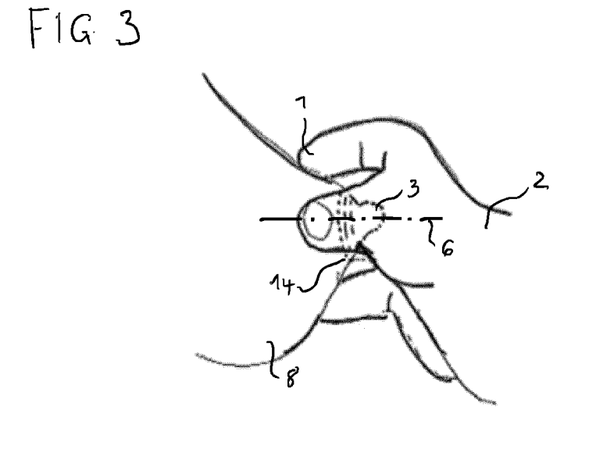
FIG. 3 an application of the pointed finger method.

In order to cause lactation without an infant, various methods are shown in FIGS. 1 to 3. These consist of a "thumb-over-finger-under method", as shown in FIG. 1, a "two-to-ten-fingers method", as shown in FIG. 2, and a "five-finger method", as shown in FIG. 3. The methods of FIG. 1 and FIG. 2 are described here as "spread finger methods"; the method of FIG. 3 is described as a "pointed finger method". With both methods, a rapid and sustained ejection of milk is physiologically obtained.

In the spread finger method, the fingers 1 of one hand 2 are held radially to the nipple 3, i.e. essentially parallel to the radial line 4 or tangentially thereto, i.e. essentially parallel to a tangential line 5. In the pointed finger method, the fingertips 1 of the hand 2 are held axially to the nipple 3, i.e. essentially parallel to the axis 6, so that in this way, a milking pressure can be exerted on the nipple 3 and the adjoining regions through a wall 20 surrounding the receptacle 9. In both methods, the receptacle 9 can be deformed from outside with the fingers 1, wherein the application of a mechanical pressure corresponds to stimulation by an infant's lips and jaw. The inner sealing cuff 15 in this regard sits on the breast 8, in particular In the region of the areola 14, and seals the receptacle 9 against the breast 8. The exertion of milking pressure compresses the receptacle 9, some air escapes from the receptacle and a negative pressure or a slight vacuum is formed. This corresponds to suckling by an infant. In this manner, by means of the baby's mouth simulator in accordance with the invention, all of the important factors for bringing about lactation in a natural manner and with a characteristic emotional feedback are simulated.

Figure 10:
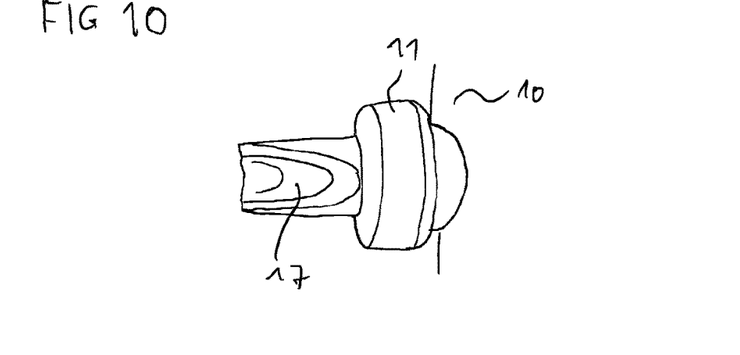

As can be seen in FIGS. 4 to 7, the baby's mouth simulator 7 for the female breast 8 has a receptacle 9 for the lactated milk. The receptacle 9 is provided with an opening 10 which is closed with a valve 11 which is configured as a one-way valve, as can be seen in FIG. 10.

Furthermore, the baby's mouth simulator 7 is provided with a milking cuff 12 which has a flexible part 13, with which the baby's mouth simulator 7 can be positioned and sealed at least on the areola 14 of the female breast 8. Furthermore, the flexible part 13 is configured such that a manual milking pressure bringing about lactation can be exerted on at least the nipple 3 of the female breast 8 or on the areola 14.

By means of the flexible part 13, the female breast 8 can be gripped with the fingers 1 of one hand 2 in a manner such that a manual milking pressure which brings about secretion can be exerted on the female breast 8 whereupon, by means of the mother's fingers 1, in contrast to a conventional pump, a rhythmic, precisely measurable milking pressure can be exerted on the areola 14 or the adjoining region of the breast and both a stimulation of the nerves as well as effective emptying can be carried out. In this manner, in a physiological manner, a rapid and sustained expression of milk can be obtained. If the breast 8 is swollen, in particular with spurting of the milk or a blockage, in this event, a gentle pressure can also be exerted on the areola 14 for a minute in order to move the blocking lymph fluid away. The milking pressure which is exerted also acts to significantly increase the quantity of milk which can be obtained over the same period. In addition to saving time, when used frequently, this leads to achieving almost complete potential milk production from the mother.

As can be seen in the drawings, the milk cuff 12 is configured as a double cuff, wherein an inner sealing cuff 15 which seals the receptacle 9 against the areola 14 when used appropriately and a fixation cuff 16 which mechanically fixes the baby's mouth simulator 7 on the breast 8 when used appropriately are provided. The fixation cuff 16 is larger in construction than the sealing cuff 15 and surrounds the sealing cuff 15.

Figure 4:
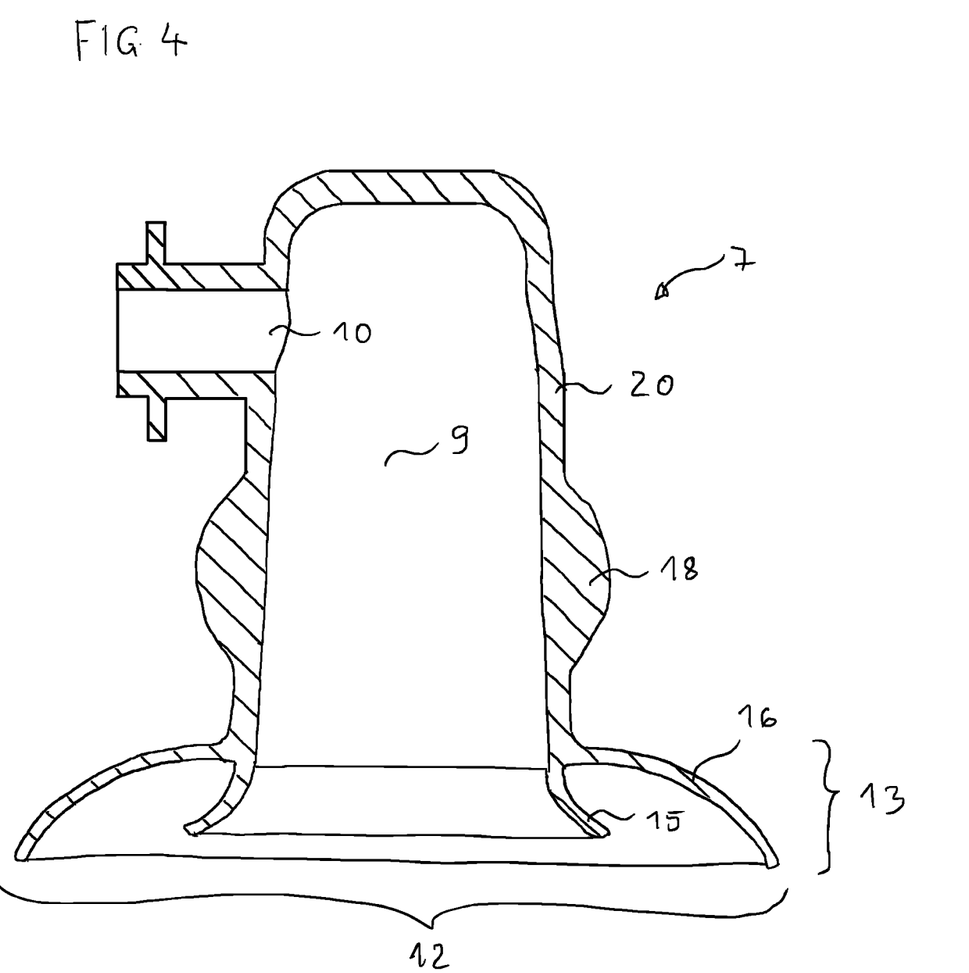
FIG. 4 a cross section through a baby's mouth simulator in accordance with the invention, FIG. 5 a first perspective view of the baby's mouth simulator in accordance with FIG. 1, FIG. 6 a second perspective view of the baby's mouth simulator in accordance with FIG. 1, FIG. 7 a third perspective view of the baby's mouth simulator in accordance with FIG. 1, FIG. 7a a baby's mouth simulator in the view corresponding to FIG. 7, as a multi-part embodiment with different materials, FIG. 7b a configuration of the opening in a connecting piece with a flange for placing on bottles, FIG. 7c a configuration of the opening in a connecting piece with a flange for placing on bottles, with a ventilation opening, FIG. 7d a configuration of the opening in a connecting piece with a flange for screwing onto bottles, FIG. 8 a first perspective view of a baby's mouth simulator with protrusions, FIG. 9 a second perspective view of a baby's mouth simulator with protrusions, FIG. 10 a valve in the form of a one-way valve, FIG. 11 a first perspective view of a baby's mouth simulator with protrusions and nipple protecting member, FIG. 12 a second perspective view of a baby's mouth simulator with protrusions and nipple protecting member, FIG. 13 a collecting container assembly, FIG. 14 an embodiment of a baby's mouth simulator for use in an adapter in accordance with FIG. 15, in cross section, FIG. 15a baby's mouth simulator in accordance with FIG. 14, in use in a rigid funnel of a conventional milk pump, FIG. 16 an embodiment with an adapter for connecting the baby's mouth simulator to a collecting container of a pump set which is known per se, FIG. 17 an embodiment with the adapter as in FIG. 16, for connection to a conventional milk pump, as shown in FIG. 15, and FIG. 18 a baby's mouth simulator for small quantities of milk.
Figure 5:
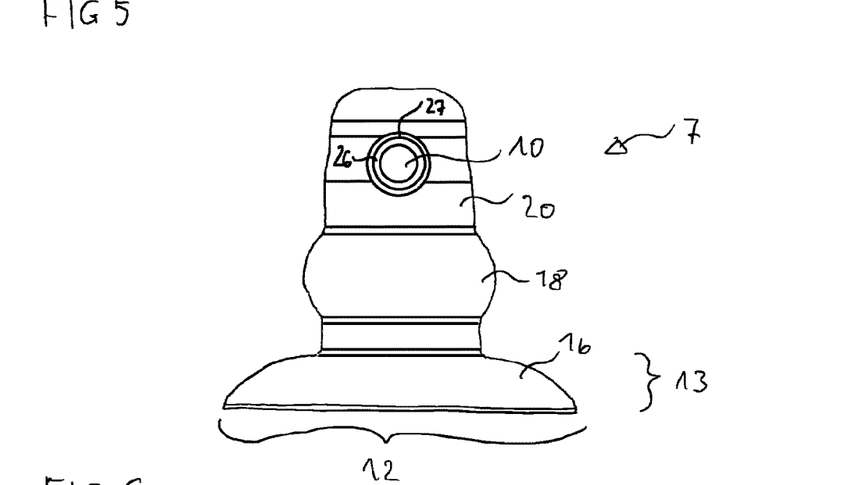
Figure 6:
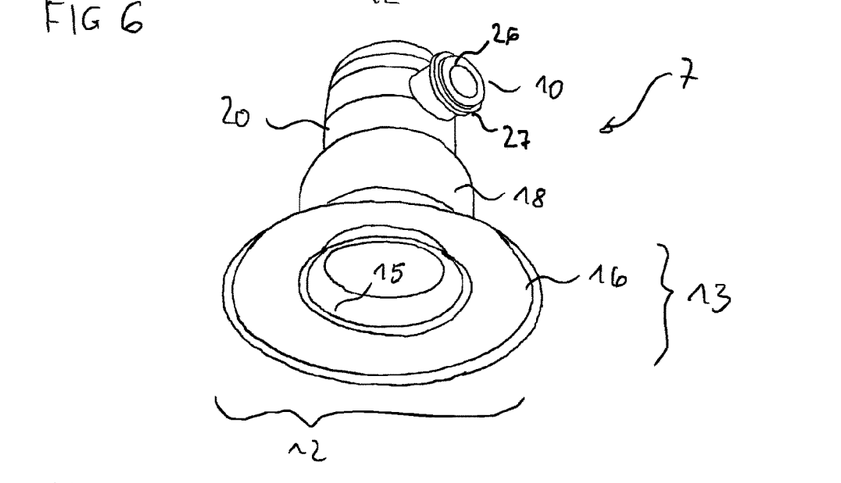

The receptacle 9 is configured as a vacuum chamber by means of the one-way valve 11 or a closing cap.

In both methods, the receptacle 9 can be deformed from outside with the fingers. In this case, the inner sealing cuff 15 sits on the breast 8, in particular in the region of the areola 14. The deformation compresses the receptacle 9. This causes some air to escape from the receptacle 9 and a negative pressure or a slight vacuum is produced.

The outer fixation cuff 16 does not need to carry out a sealing action. Rather more, it serves to carry out mechanical fixing, wherein the hand 2 or the finger 1 presses the fixation cuff 16 onto the breast 8. The baby's mouth simulator 7 is then fixed thereby.

The valve 11 is configured as a one-way valve. As can be seen in FIG. 10, this valve has sealing lips 17 which are forced apart by escaping air when the receptacle 9 is compressed, thereby opening a passage for the escaping air. When the fingers 1 let go of the receptacle 9, because of the flexible material, this has a tendency to return to its original shape, whereupon the vacuum is produced. If the vacuum is then formed in the receptacle 9, the external air pressure presses the sealing lips 17 together and the opening 10 of the receptacle 9 is closed.

In order to mechanically protect the nipple 3, a reinforcing ring 13 is provided which surrounds the receptacle 9.

Figure 7:
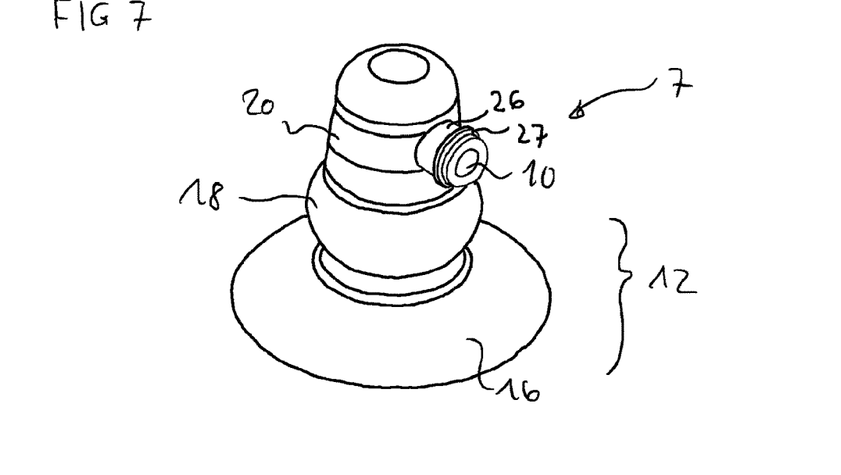
Figure 7A:
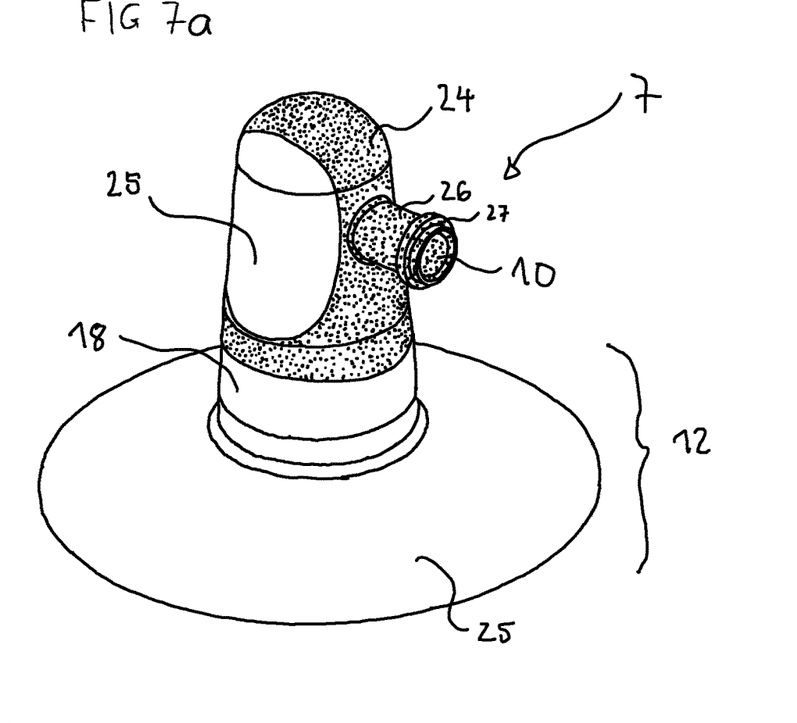

FIG. 7a shows an embodiment in which the baby's mouth simulator consists of at least two different materials. Thus, a first region 24, shown shaded with dots in the drawing, is produced from a material which is stiffer compared with a second region 25.

Figure 7B:
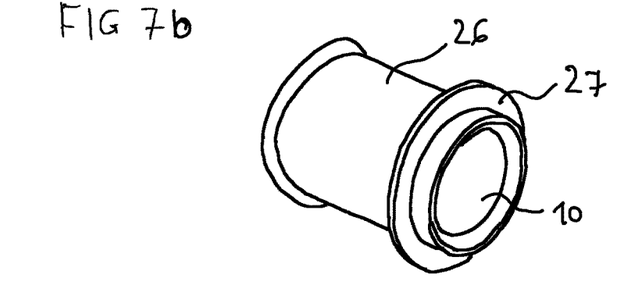

FIG. 7b shows an embodiment of the opening in a connecting piece 26. The connecting piece 26 is provided with a flange 27 for insertion of a bag, not shown. Thus, a rim of the bag can be drawn over the flange and fastened to the connecting piece 26, simultaneously sealing it off.

Figure 7C:
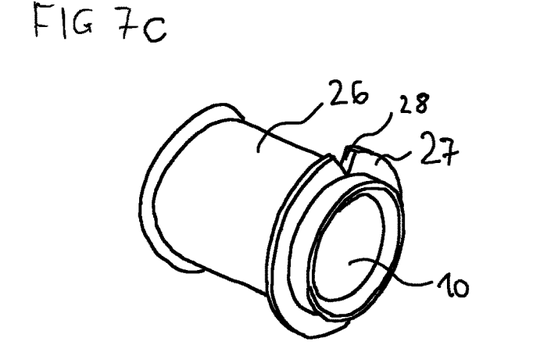

As can be seen in FIG. 7c, the border of the flange 27 is provided with a notch 28. When the bag is deployed, this forms an opening with the border of the bag through which the air can escape from the bag in order to equilibrate the pressures as the milk flows in.

Figure 7D:
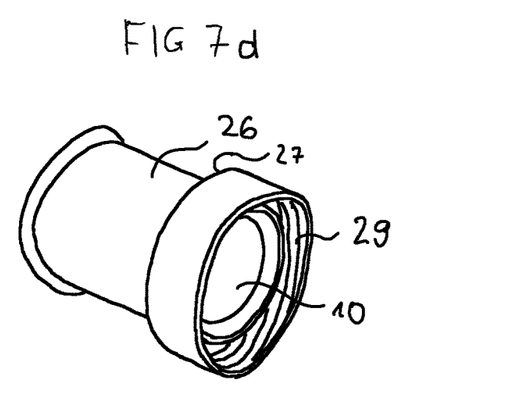
Figure 8:
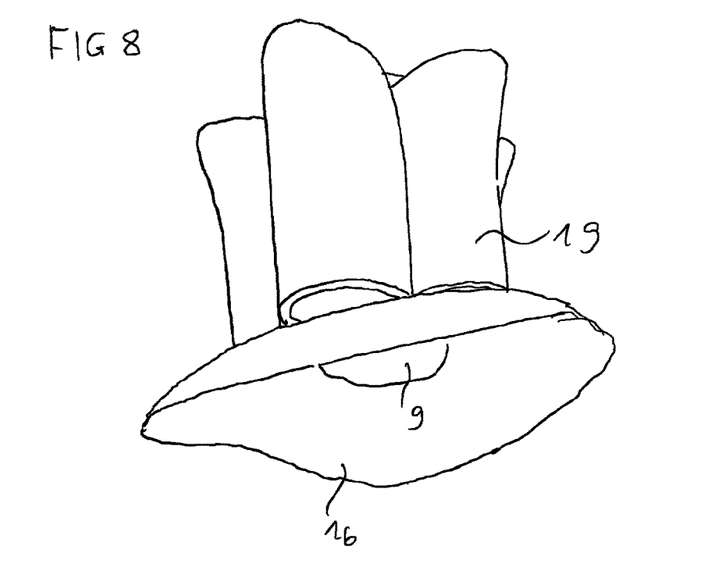
Figure 9:
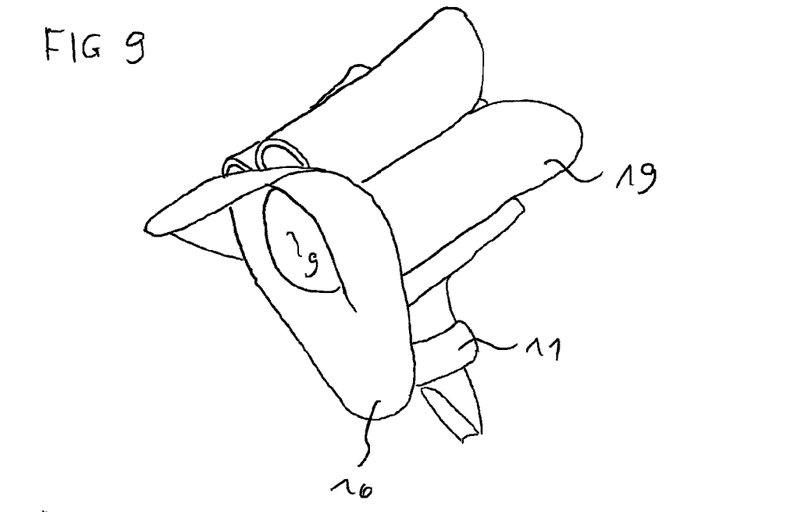

As can be seen in FIG. 7d, the flange is provided with a threaded fitting 29 which has an internal thread into which an external thread of a flange which is not shown can be screwed.

As can be seen in FIGS. 6, 9, 11 and 12, the baby's mouth simulator 7 is configured such that the outside of the receptacle 9 is provided with protrusions 19, in which at least parts of the finger 1 of a hand 2 can be accommodated. By means of these protrusions 19, the female breast 8 or the areola 14 can be gently cupped by the fingers 1 of the hand 2 through the wall 20 of the receptacle 9 and a manual milking pressure which brings about lactation can be exerted with the fingers on the nipple and the adjoining regions.

At least the fingertips 1 of the hand 2 can be accommodated in the protrusions 19, wherein the protrusions 19 surround the receptacle 9.

Figure 11:
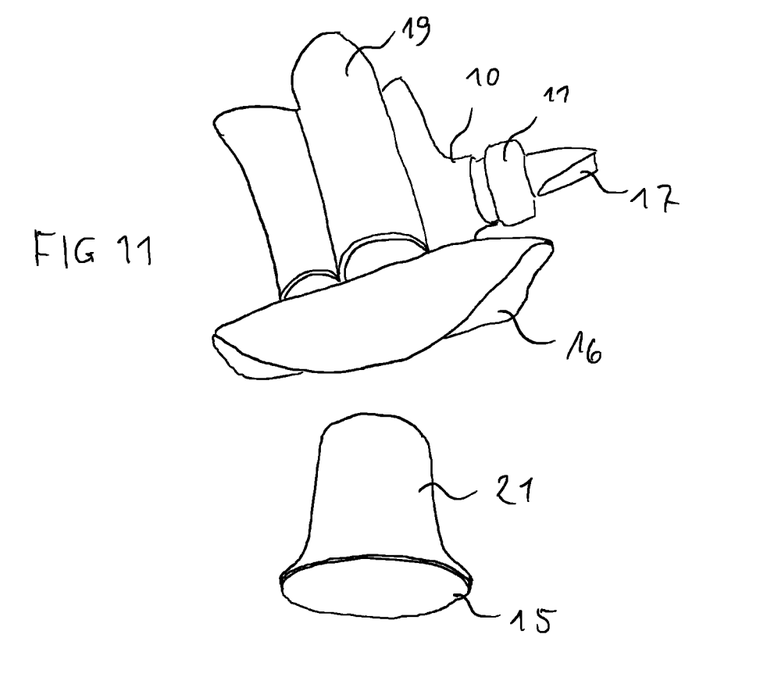
Figure 12:
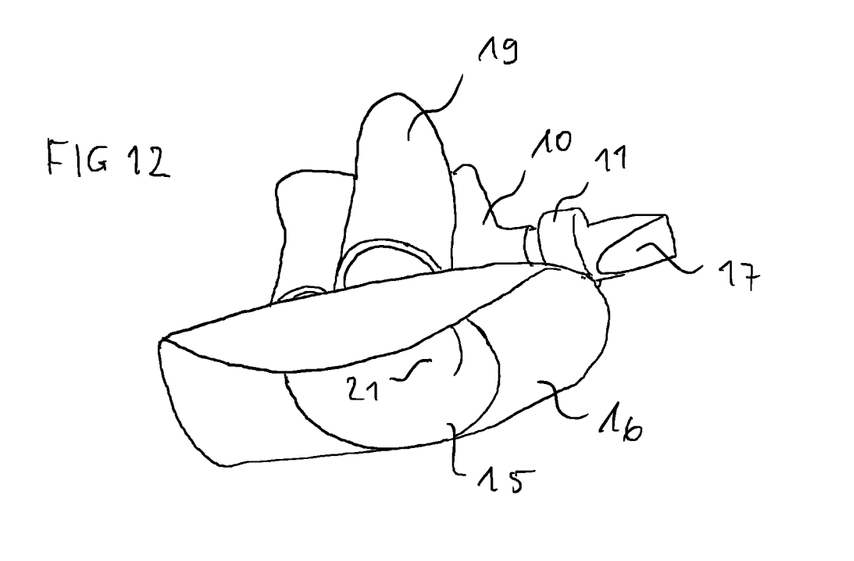

In the exemplary embodiment which is shown in FIGS. 11 and 12, a nipple protecting member 21, produced from a material which is stiffer compared with the milking cuff 12 or the wall 20 of the receptacle 9, is provided and which can be inserted into the receptacle 9. This nipple protecting member 21 offers—in similar manner to the reinforcing ring 18 already described above—protection of the nipple 3 from too fierce a milking movement. This nipple protecting member 21 can be inserted into a baby's mouth simulator 7 provided with external protrusions 19 for the pointed finger method, because in this solution, it is not sensible to provide a solid reinforcing ring 18.

The nipple protecting member 21 has to be inserted and sealed into the receptacle 9, whereupon the sealing cuff 15 is connected to the nipple protecting member 21.

Figure 13:
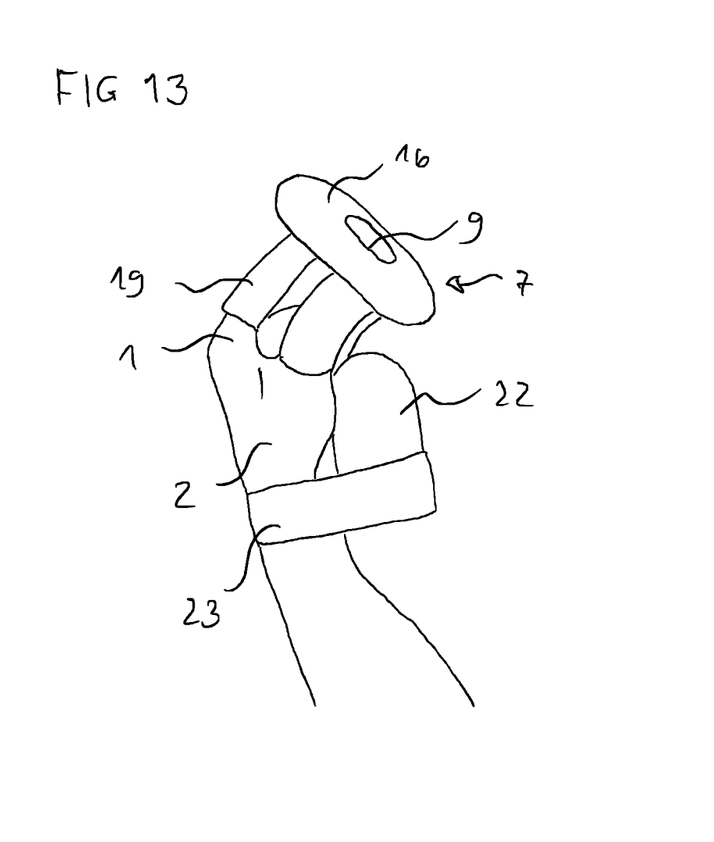

As can be seen in FIG. 13, a collecting container 22 may be connected to the receptacle 9. The lactated milk can flow out into this collecting container 22. To this end, the collecting container 22 is provided with an arm cuff 23, in particular for fastening to the wrist. The connection of the collecting container 22 to the receptacle 9 may be made by means of a screw or push-fit connection.

For small quantities of milk, it may also be possible to close off the receptacle 9 with a closure. In this case, the valve 11 may also be dispensed with.

Figure 14:
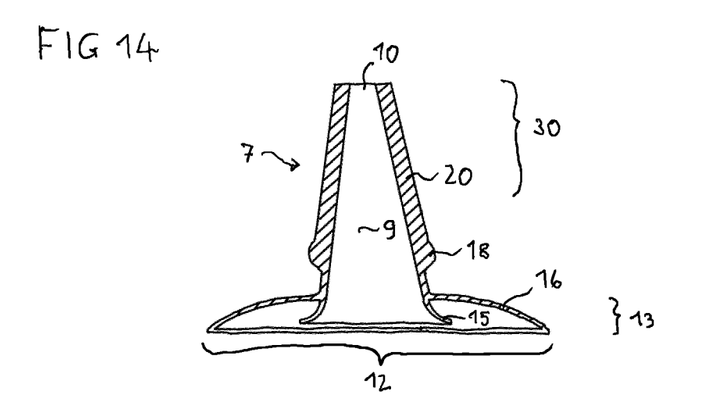

FIG. 14 shows another embodiment for connecting the receptacle 9 to the collecting container 22. The construction of the baby's mouth simulator in principle corresponds to the construction of FIG. 5. Here, however, the opening 10 is disposed on the side of the wall 20 which is facing away from the milking cuff, and the outside of the wall 20 is conical in shape at least in a region 30 disposed at the opening 10.

Figure 15:
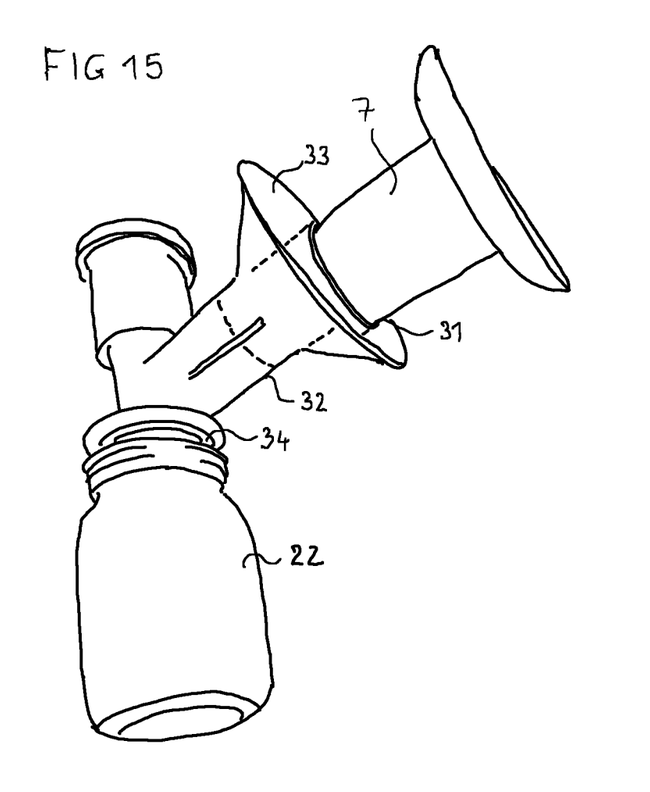

As can be seen in FIG. 15, this region 30 serves for insertion into an opening 31 of a rigid funnel 32, 35 and 34 of a conventional milk pump.

In this embodiment, the negative pressure is produced by means of an electric milk pump (not shown). In a milk pump without the intervention of the invention, normally, the collar 33 is placed onto the region of the nipple 3. With the aid of the invention, the baby's mouth simulator 7 is now "interposed". The mother can now stimulate, massage and at the same time make milking finger movements the breast using the baby's mouth simulator 7 with the aid of the adapter 32 during the pumping procedure. The inner cuff 15 serves to seal the electrically produced negative pressure against the breast. The outer cuff 16 serves to fix the adapter 32 on the breast and allows the fingers to make the milking movements. The nipple protecting ring 18 keeps the nipple region open and thus also ensures freedom from pain and also dilates the nipple to reinforce milk expression.

Figure 16:
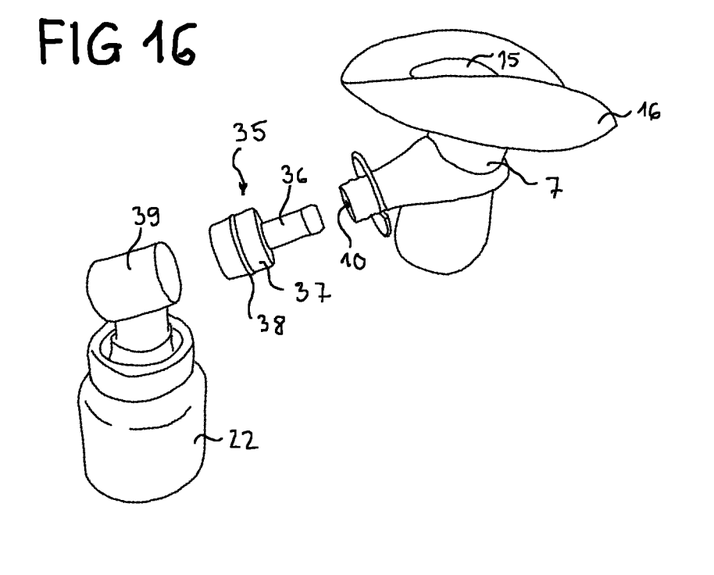

FIG. 16 shows the embodiment with a plug-in adapter 35. It has an insertion tube 38 which can be inserted into the opening 10 of the baby's mouth simulator. The insertion tube 36 is provided with a through opening with an insertion piece 37 the outside of which is provided with an O ring 38. By shaping the insertion piece 37 appropriately, it is possible to connect the baby's mouth simulator to collecting containers 22 from other manufacturers, thereby enabling universal use. In the form shown here, the insertion piece is configured in a manner such that it can be inserted into the tube connector 39 of a pump set from a different manufacturer.

Figure 17:
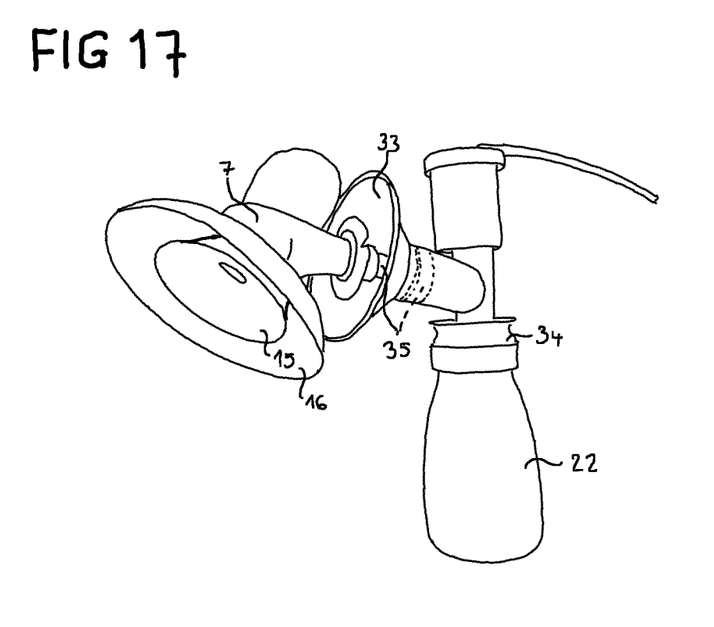

FIG. 17 shows a baby's mouth simulator 7 mounted on a milk pump as already illustrated in FIG. 15, and the use of a plug-in adapter 35. In this regard, the insertion piece has been designed in a manner such that it is compatible with the opening of the collar 33 and can be inserted therein.

Figure 18:
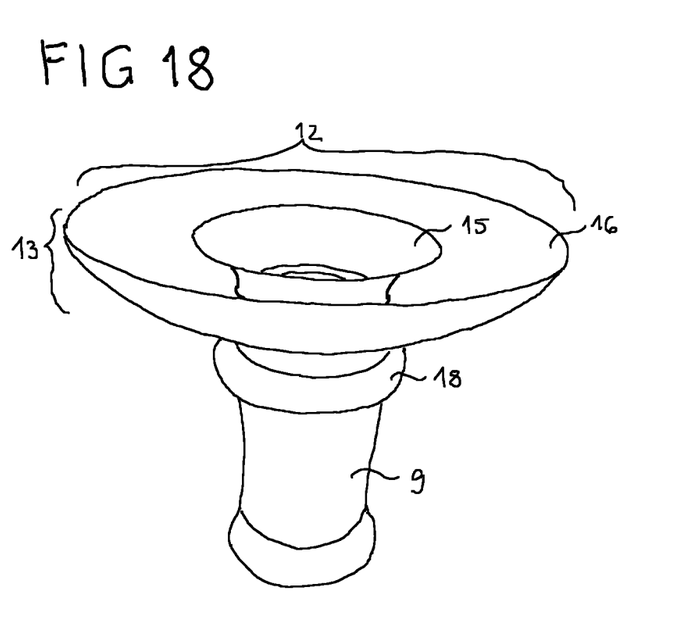

FIG. 18 shows a baby's mouth simulator 7 for smaller quantities of milk. Here, the receptacle 9 does not have an opening 10. This baby's mouth simulator is set with the sealing cuff 35 on the breast, compressed slightly, whereupon a negative pressure is generated, and held on by the fixation cuff 16. The milk which is expressed by the milking movement via the milking cuff 12 and the negative pressure is simply collected in the receptacle 9. If this is full, or no more lactation occurs, then the baby's mouth simulator is removed and the receptacle 9 is emptied.

LIST OF REFERENCE NUMERALS 1 fingertip, finger
2 hand
3 nipple
4 radial line
5 tangential line
6 axis
7 baby's mouth simulator
8 breast
9 receptacle
10 opening
11 valve
12 milking cuff
13 flexible part
14 areola
15 inner sealing cuff
16 fixation cuff
17 sealing lip
18 reinforcing ring
19 protrusion
20 wall
21 nipple protecting member
22 collecting container
23 arm cuff
24 first region
25 second region
26 connecting piece
27 flange
28 notch
29 threaded fitting
30 region
31 opening
32 adapter
33 collar
34 threaded fitting
35 plug-in adapter
36 insertion tube
37 insertion piece
38 O ring
39 tube connector

The invention claimed is:

1. A baby's mouth simulator for the female breast, said mouth simulator comprising:
   a receptacle for lactated milk;
   a milking cuff having a flexible part, with which the baby's mouth simulator is configured to be positioned and sealed onto at least the nipples of the female breast and which is configured in a manner such that a manual milking pressure bringing about lactation can be exerted on the nipple and adjoining regions, wherein by way of the flexible part, the female breast can be gripped with fingers such that a manual milking pressure can be exerted on the female breast by way of the fingers;

the flexible part comprising a double cuff, the double cuff comprising:
- an inner sealing cuff configured to seal the receptacle against the areola, wherein the inner sealing cuff comprises a first free end;
- a fixation cuff configured to mechanically fix the baby's mouth simulator on the breast without having a sealing function, wherein the fixation cuff comprises a second free end;

the receptacle being configured as a vacuum chamber; and
the fixation cuff being larger than the sealing cuff and surrounding the sealing cuff,
wherein a reinforcing ring is provided which surrounds the receptacle;
wherein the reinforcing ring is non-detachably connected to the inner sealing cuff;
wherein the reinforcing ring is configured to provide mechanical protection of the nipple.

2. The baby's mouth simulator as claimed in claim 1, wherein:
the receptacle has an opening fitted with a valve configured as a lip valve.

3. The baby's mouth simulator as claimed in claim 1, wherein:
the baby's mouth simulator is constructed in two or more parts.

4. The baby's mouth simulator as claimed in claim 1, wherein:
the flexible part is constructed from a soft resilient material.

5. The baby's mouth simulator as claimed in claim 3, wherein:
the parts of the baby's mouth simulator comprise different materials that are connected together.

6. The baby's mouth simulator as claimed in claim 1, wherein:
a collecting container is configured to be connected to the receptacle.

7. The baby's mouth simulator as claimed in claim 2, wherein:
a collecting container is configured to be connected to the receptacle; and
the valve or a second valve is disposed between the receptacle and the collecting container.

8. The baby's mouth simulator as claimed in claim 7, further comprising:
an arm cuff configured for the collecting container.

9. The baby's mouth simulator as claimed in claim 1, further comprising:
a collecting bag having a mechanical vibrator.

10. The baby's mouth simulator as claimed in claim 2, wherein:
the valve is a one-way valve.

11. The baby's mouth simulator as claimed in claim 8, wherein:
the arm cuff is configured for fastening the collection container to the wrist or to the forearm.

* * * * *